United States Patent [19]

Binder

[11] Patent Number: 5,298,401
[45] Date of Patent: Mar. 29, 1994

[54] PROCESS FOR THE QUANTITATIVE DETERMINATION OF THE FUNCTION AND ANTIGENIC CONCENTRATION OF A SUBSTANCE CONTAINED IN A BIOLOGICAL LIQUID

[76] Inventor: Bernd Binder, Freyung 6, A-1010 Vienna, Austria

[21] Appl. No.: 310,724
[22] PCT Filed: May 5, 1988
[86] PCT No.: PCT/AT88/00027
 § 371 Date: Jan. 5, 1989
 § 102(e) Date: Jan. 5, 1989
[87] PCT Pub. No.: WO88/08883
 PCT Pub. Date: Nov. 17, 1988

[30] Foreign Application Priority Data

May 5, 1987 [AT] Austria ............................ 1127/87

[51] Int. Cl.⁵ ............. G01N 33/53; G01N 33/566; C12Q 1/56; C12N 9/74
[52] U.S. Cl. ............................ 435/7.4; 435/7.92; 435/13; 435/214; 435/215; 435/217; 436/501; 436/512; 436/518; 436/819
[58] Field of Search ............. 436/518, 501, 572, 819; 435/7, 13, 215, 214, 217, 7.4

[56] References Cited

U.S. PATENT DOCUMENTS

| | | |
|---|---|---|
| Re. 29,169 | 0/0000 | Schuurs et al. |
| Re. 31,006 | 0/0000 | Schuurs et al. |
| 4,016,043 | 0/0000 | Schuurs et al. |
| 4,563,420 | 1/1986 | Verheijen ............... 435/13 |
| 4,629,694 | 12/1986 | Harpel ................... 435/7.1 |
| 4,690,890 | 9/1987 | Loor et al. ............. 435/7.4 |
| 4,707,443 | 11/1987 | Nelson et al. ......... 436/501 |
| 4,849,353 | 7/1989 | Harpel ................... 435/7.4 |

FOREIGN PATENT DOCUMENTS

| | | |
|---|---|---|
| 0094720 | 11/1983 | European Pat. Off. |
| 0141263 | 5/1985 | European Pat. Off. |
| 896253 | 3/1983 | France |
| WO8601411 | 3/1986 | PCT Int'l Appl. |
| 1549069 | of 0000 | United Kingdom |

OTHER PUBLICATIONS

Chap. 12, *Immunochemistry* (Ed Weir et al. pp. 12.8 & 12.9 (1986).
Parham, P., "Preparation and Purification of Active Fragments ... ", *Immunochemistry*(Ed Weir et al.), pp. 14.1, 14.2 & 14.7 (1986).
Kroninger et al, Chem Absts. 104:182106k (1986).
Friguet et al., "A Convenient Enzyme Linked Immunosorbent Assay for Testing Whether Monoclonal Antibodies Recognize the Same Antigonic Site," Inj Immunoenzymatic Techniques, ed. S. Auramuas et al., Elsevior Science Publishers B.V., Amsterdam, Neth., 171-174 (1983).
C. Kluft, Tissue Plasminogen Activator, CRC (1988) Boca Raton, Florida, p. 102.
C. W. Francis et al, Physiologic Regulation and Pathologic Disorder of Fibrinolysis, J. B. Lippincott Co. Philadelphia, 1987.
Plasminogen Activators, North-Holland Publishing Co. Amsterdam, N.Y. Oxford 1977.
The Plasminogen-Plasmin Enzyme System, p. 349, Robbins, J.B. Lippincott Co. Philadelphia, 1987.

(List continued on next page.)

*Primary Examiner*—Christine M. Nucker
*Assistant Examiner*—M. Patrick Woodward
*Attorney, Agent, or Firm*—Herbert Dubno; Jonathan Myers

[57] ABSTRACT

In a process for the quantitative determination of the function and antigenic concentration of a substance contained in a biological liquid, the substance is immobilized, the function is determined by the addition of a specific substrate which is then removed by washing, and in a subsequent step the immunological concentration of the bound substance is determined using an appropriate specific detector system with or without the use of an antibody.

6 Claims, 5 Drawing Sheets

OTHER PUBLICATIONS

Chem. Abstracts 104:182106k (1986).

Bergemyer, Methods of Enzymatic Analysis, vol. V, pp. 425–433.

Bidwell, V. A. et al, The Enzyme Linked Immunosorbent Assay (Elisa) p. 3 (1977).

Travis, Jeffrey C., Clinical Radioimmunoassay... State of the Art 1st Edition (1980).

Nakamura, R. M. et al, Immunoassays in the Clinical Laboratory (1978).

Langone, John J., Methods in Enzymology, vol. 73, Immunochemical Techniques, Part B (1981).

Langone, John J., Methods in Enzymology, vol. 92, Immunochemical Techniques, Part E (1983).

Lorand, Laszlo, Methods in Enzymology, vol. XLV, Proteolytic Enzymes, Part B (1976).

PROCESS FOR THE QUANTITATIVE DETERMINATION OF THE FUNCTION AND ANTIGENIC CONCENTRATION OF A SUBSTANCE CONTAINED IN A BIOLOGICAL LIQUID

BACKGROUND OF THE INVENTION

The concentration of biologically significant substances in various liquids, such as blood, urine, fluids or others, is usually determined through two totally different methods. On the one hand through various determined (antigenic concentration). Such methods include made known (antigenic concentration); such methods include the radioimmunoassay (Travis, J. C., Clinical Radioimmunoassay, State of the Art, Radioassay, Ligand assay Publishers, Anaheim, Calif. 1980), the enzyme-linked-immunosorbent-assay (Nakamura, R. M., Dito, W. R. Tucker II E. S., Immunoassays in the Clinical Laboratory, Laboratory and Research Methods in Biology and Medicine, Vol. 3, Alan A. Liss Inc., New York, 1979; Voller, A., Bidwell, D. E., Bartlett, A., The Enzyme Linked Immunosorbent Assay - ELISA, The Authors, 1979, London; Langone,J. J., Van Vunakis, H., Methods in Enzymology, Immunochemical Techniques Part E, 1983, Academic Press; further Schuurs et al., U.S. Pat. No. 29,169 and Schuurs et al. , U.S. Pat. No. 4 016 043 )or coarse methods (Nakamura, R. M., Dito, W. R. Tucker III, E. S. Immunoassays in the Clinical Laboratory, Laboratory and Research Methods in Biology and Medicine, Vol. 3, Alan R. Liss Inc., New York, 1979; Langone, J. J., Van Vunakis, H., Methods in Enzymology, Immunochemical Techniques Part B, 1981, Academic Press), such as immunonephelometry, radial immunodiffusion or other appropriate immuno-precipitation processes. With the aid of immunological determination, it is possible to establish the concentration of a substance. However, it is impossible to draw any conclusion as to the function of this so-established substance. It has been proven frequently that, in various cases, in a normally immunologically determinable concentration, the function of this molecule did not correspond to the one immunologically determined and often was well below the normal value. As is the case with such molecules in proteins, having a precise enzymatic function or a carrier or cofactor function or the like in the body fluid and whose function is impaired by modifications in certain molecular fragments or which are inhibited by fixation to inhibitors.

The second possibility to establish the concentration of a certain substance in body fluids is the determination of the function of this substance (Bernmeyer, H. U., Methods of Enzymatic Analysis, Vol. 5 Verlan Chemie, 1984). Thereby, various systems are used, most of them being based on an enzyme reaction and which measure the enzymatic activity of the desired substance (Lorand, L., Proteolytic Enzymes, Methods in Enzymology, Vol. 45, 1976, Academic Press). By selecting specifically suitable substrates (e.g. high-molecular natural substrates, which are transformed by enzymes, such as fibrinogen for its enzyme thrombin, fibrin as substrate for plasmin, plasminogen as substrate for plasminogen activators, kininogen as substrate for kallikrein , but also low-molecular substrates, which contain the specific peptide compound for the respective enzyme and whose decomposition can lead, for instance, to a color reaction) and suitable determination criteria (thereby in the case of active enzyme formation, in the first stage the respectively formed enzymes are measured, respectively in the case of low-molecular substrates, the colored products, resp. newly formed or lost characteristics of substrates, such as the capability to form a bond with certain substances. An example of the los of such capability is the binding of the active plasminogen activator-inhibitor to its binding protein, whereby this binding capability is lost in the deactivation of the plasminogen activator-inhibitor. Further examples for these assaying processes involve binding to specific inhibitors, transfer proteins or other binding proteins, which can be correspondingly marked and be traced through a coupled reaction. It is possible to obtain a relatively high specificity for the determined substance; however, it is impossible to indicate a measured value with absolute specificity, since normally a multitude of enzymes or other substances catalyze the same or a similar reaction on the same substrates, although with different speeds. An example of same is the activation of plasminogen to plasmin through plasminogen activators, whereby at least two main plasminogen activators are present in the body fluid, each of them splitting the same bond in the plasminogen, whereby an identical plasmin is formed. Thus, with the functional method it is not possible to perform the quantitative analysis of a precisely defined substance; it is possible only to ascertain a functional defect of the entire system.

SUMMARY OF THE INVENTION

In contrast to the two above-described groups of methods, with the present invention it is possible, on the one hand, to measure the functional activity of a precisely determined substance, as well as subsequently thereto, from the same sample, to quantitatively assess the immunological concentration of the same substance. The method of the invention involves a first step, wherein the unknown substance specifically either immobilized on a surface through corresponding interaction with a binding protein (e.g. fibrin, cofactors, but also lipides, lektine) or with a specific antibody, preferably a monoclonal antibody, and in this way is removed for the sample. Then the so-bound substance is examined through a corresponding suitable substrate (such as plasminogen activation and measuring of the resulted plasmin with a low-molecular plasmin substrate, a low-molecular substrate in itself, the activator to be inhibited for an inhibitor) as to its function, to assay it quantitatively, and subsequently, through a second specific analysis step, e.g. an antibody or a binding protein, to measure the total antigenic concentration of the bound substance.

The advantage of this method is twofold: on the one hand, in the same sample both the antigenic concentration and the function can be examined, and, on the other hand, in the function test, only the function of the specifically bound enzyme or of the substance is examined and not the functional activity of the entire specimen.

Further, the invention consists in that the substance contained in the biological liquid is immobilized by binding it to a plate surface with the aid of a polyclonal or a monoclonal antibody.

Furthermore, the invention consists in that, starting from a plasma or urine specimen, the plasminogen activator contained therein is immobilized and in the first step, the plasmin formation is measured through added plasminogen, and that in the second analysis step, the immunological concentration of the bound plasminogen activator is determined with the aid of a monoclonal antibody, which has been peroxidase -marked,used as a detector system.

Finally, the invention consists in that a specific binding protein or another substance which specifically binds with the desired immobilized antigen, is used as a detector system. This can be for instance a natural or synthetic inhibitor, a natural or synthetic binding protein, a cofactor or a lipid.

The following examples, which have a non-limitative character, explain possible embodiments of the process according to the invention.

EXAMPLE 1

System for the Determination of the Function and Antigen of the Tissue Plasminogen Activator in Biological Liquid. Micro Elisa plates are treated with 100 μl per dish of 0.035 M sodium bicarbonate-buffer, pH 9.6, which contains 40 μg per ml 20, 10 or 5,μg/ml of a cleansed monoclonal antibody against the tissue plasminogen activator (MPW1VPA), for 12 hours at 4° C. After that, these are washed three times with 300 μl per dish PBS, containing 0.5% Tween. The remaining binding sites on the polystyrene plate are saturated at room temperature for 4 hours through the addition of 100 μl per dish of a 1% -25% bovine serum albumin solution in PBS, whereafter the plates are again washed as indicated above. Hereafter, the plates can either be dried, lyophilised or preserved in any other suitable way.

In order to perform the analysis, after a single washing as above with 100 μl of a tPA-containing solution, if necessary diluted in PBS, containing 0.5% bovine serum albumin and 0.1% tween 80 is added. The plates are kept for 2 hours at 4° C., whereby the time or the temperature can vary. After that, the plates are again washed and then 100 μl per dish of a solution having a suited plasmin substrate, for instance H-D-Val-Leu-Lys-pNA in a concentration of 0.6 mM and three different concentrations of the natural substrate Glu-plasminogen (750 nM, 375 nM and 187 nM final concentration) is added, and also cyanbromide fragments of the fibrinogen in a concentration of 75 μg/ml. The plates are thereafter incubated in the dark for 2, 3 or 5 hours at 37° C., and thereafter the extinction is measured at 405 nm against the 495 nm reference wave-length, whereby a two-wave-length spectrophotometer, e.g. Dynateeh Microelisa Reader is used. Hereny, the function of the bound tissue plasminogen activator is examined and quantified.

Then, the plates are washed for the determination of the antigen, such as described above, and 100 μl of another monoclonal antibody directed against tissue plasminogen activator, peroxidase-marked or marked by another suitable enzyme, e.g. MPW3VPA, final concentration 0.5, 1.2, and 4 μg/ml, is added. Subsequently, the plates are incubated for 2 hours at 4° C. and washed after that a solution of 1 g per liter orthophenylenediamine in 0.11 sodium phosphate, 0.5 M citrate-buffer, pH 5.85, to which 0.03% $H_2O_2$ are added. 100 μl of this solution is added per dish. The plates are then incubated in the dark at room temperature for 30 minutes and subsequently thereto the reaction is concluded by the addition of 100 μl of a 1.5M sulfuric acid per disin. The extinctions are measured at 495 nm and at 630 nm as reference wave-length, whereby the above-mentioned photometer is used.

As a routine procedure the following values have been selected: the concentration of the first antibody equals 10 μg/ml, the concentration of the Glu-plasminogen 750 nM, the incubation time for the plasmin formation 3 hours and the concentration of the second, peroxidase-marked antibody equals 1 μg/ml.

Standard curves for t-PA activity and tPA antigen: purified tPA preparations are prepared in a concentration of 10, 5, 2.5, 1.25, 0.625, 0.3125 and 0.15 ng/ml in PBS-buffer, under the addition of 0.1% Tween 80 and 0.5% BSA, whereby also the international standard in concentrations between 0.075 5 units per ml is used. In order to prove to what extent the esterolytic activity is present in the plates, independent from the plasmin, for the first test system, also Glu-plasminogen was replaced by 0.5% serum albumin. In order to determine to what extent the unspecific binding of the second antibody influences the assay system, PBS containing 0.5% BSA, 0.01% Tween has been used instead of the t-PA containing specimen. EDTA and sodium citrate have been added for the dilution of the purified tPA, in order to study their possible influence on the standard curve.

Checking of the Effect of the Added Plasminogen Activator Inhibitor on the Assay System: Purified plasminogen activator-inhibitor has been added in a concentration of one t-PA inhibiting unit per ml to the corresponding dilutions of the purified t-PA. On the other hand, the plasminogen activator-inhibitor has also been added in the same concentration to a t-PA-dilution, which had already reacted on the plate with the first antibody. In both cases, the reaction of the plasminogen activator-inhibitor with the t-PA was performed for 30 minutes at 37° C. As a control test, the same procedure was carried out, whereby PBS containing 0.5° BSA was used instead of the plasminogen activator-inhibitor. After that, the t-PA-activity and t-PA-antigen were correspondingly determined.

Recovery Tests

The recovery tests have been performed in an undiluted, pooled plasma, with various anticoagulants and a standard curve was obtained. The plasma was a pool of individual plasma specimens, obtained from 10 healthy volunteers. 0.01 M sodium citrate, 0.02M sodium EDTA and 0.05M sodium EDTA were used as anticoagulants. In the various anticoagulant plasma specimens which were treated with t-PA, the t-PA activity and the t-PA antigen were determined. From the obtained result, 0.2M sodium EDTA was found to be anticoagulant of choice. Plasma specimens were obtained from healthy volunteers, and in these plasma specimens the concentration of the tissue plasminogen activator-antigen and the activity were determined before and after a 15-minutes venous stasis. Both determinations were carried out twice, and the specimens were anticoagulated with 0.2M EDTA, as indicated above.

Figure 1:
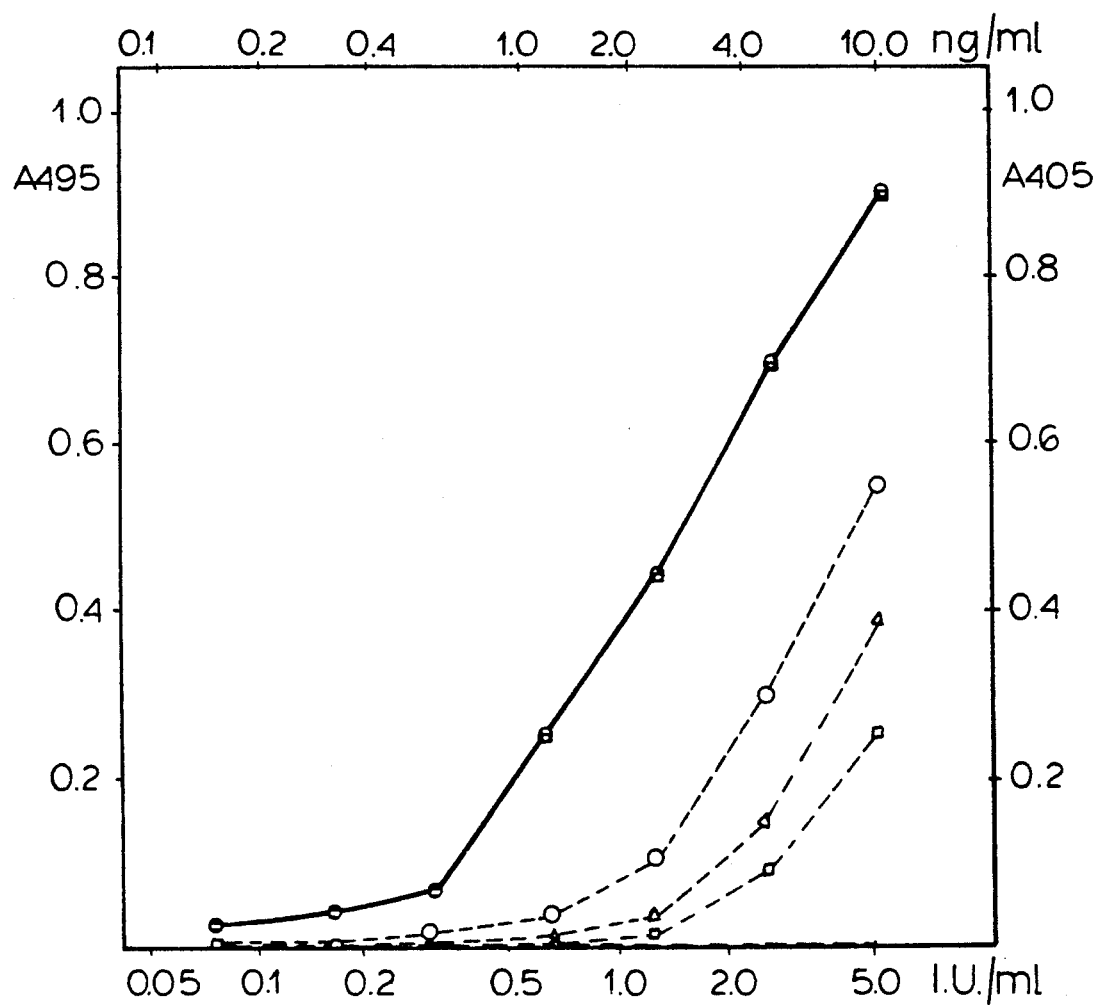
FIG. 1: Calibration Curve of the Assay System for the Determination of the t-PA-activity (interrupted line) and of the t-PA antigen (solid line). These were performed with buffer, the Glu-plasminogen in a concentration of 750 nM (open circles), 375 nM(open triangles) and 187 nM (open squares) and 0.5° BSA after 3 hours of incubation. The functional activity was measured at 405 nm and the antigen at 495 nm. These are each plotted against the international units or ng t-PA, which were added.
Figure 2:
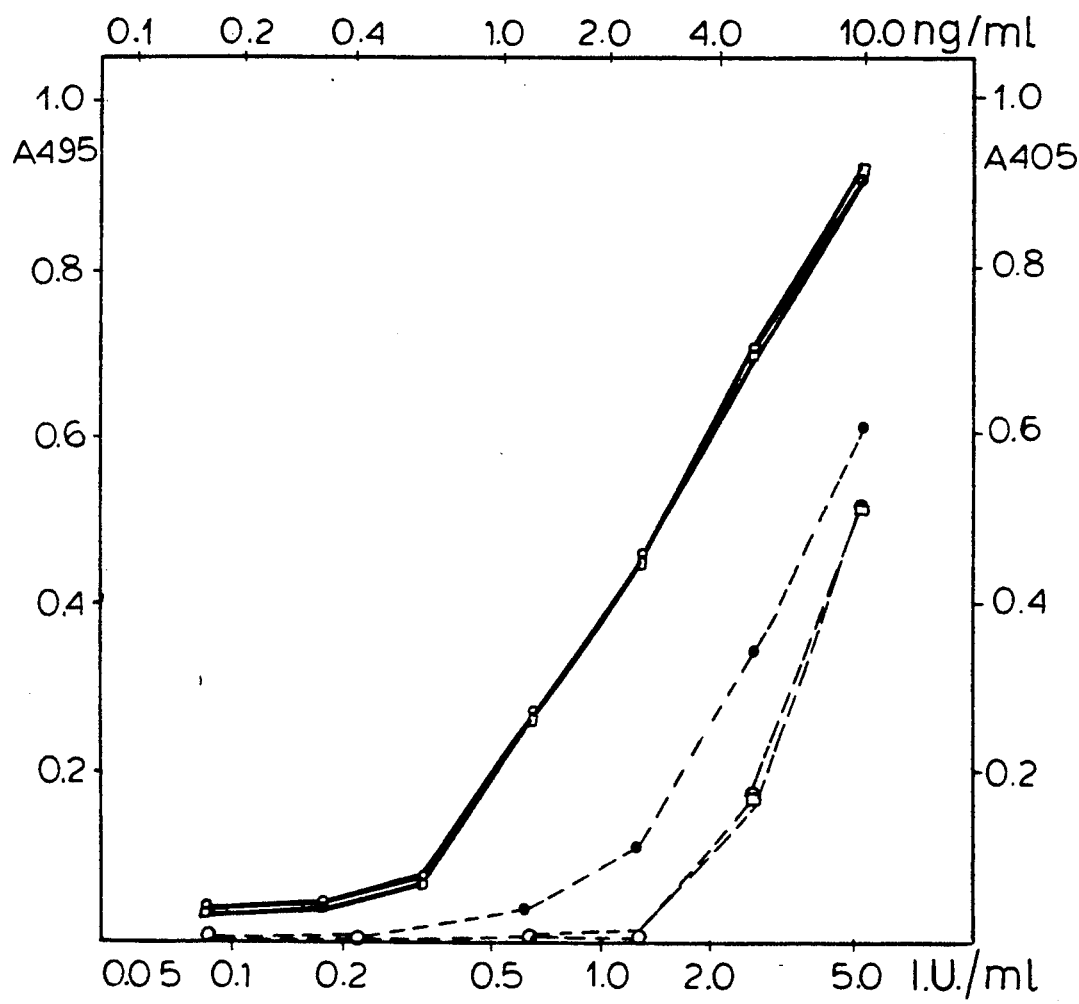
FIG. 2: Dose-effect-curve for t-PA activity. Interrupted line: t-PA antigen, solid line: after 30 minutes of preincubation at 37° C. by means of t-PA and with one unit of plasminogen activator-inhibitor before (open triangles) and after (open squares) the immobilization of the t-PA. As a control, the plasminogen activator-inhibitor was replaced by 0.05% BSA. The functional activity at 405 nm and 495 nm for antigen are correspondingly plotted on the ordinate, against the international units or ng/ml t-PA on the abcissa.
Figure 3:
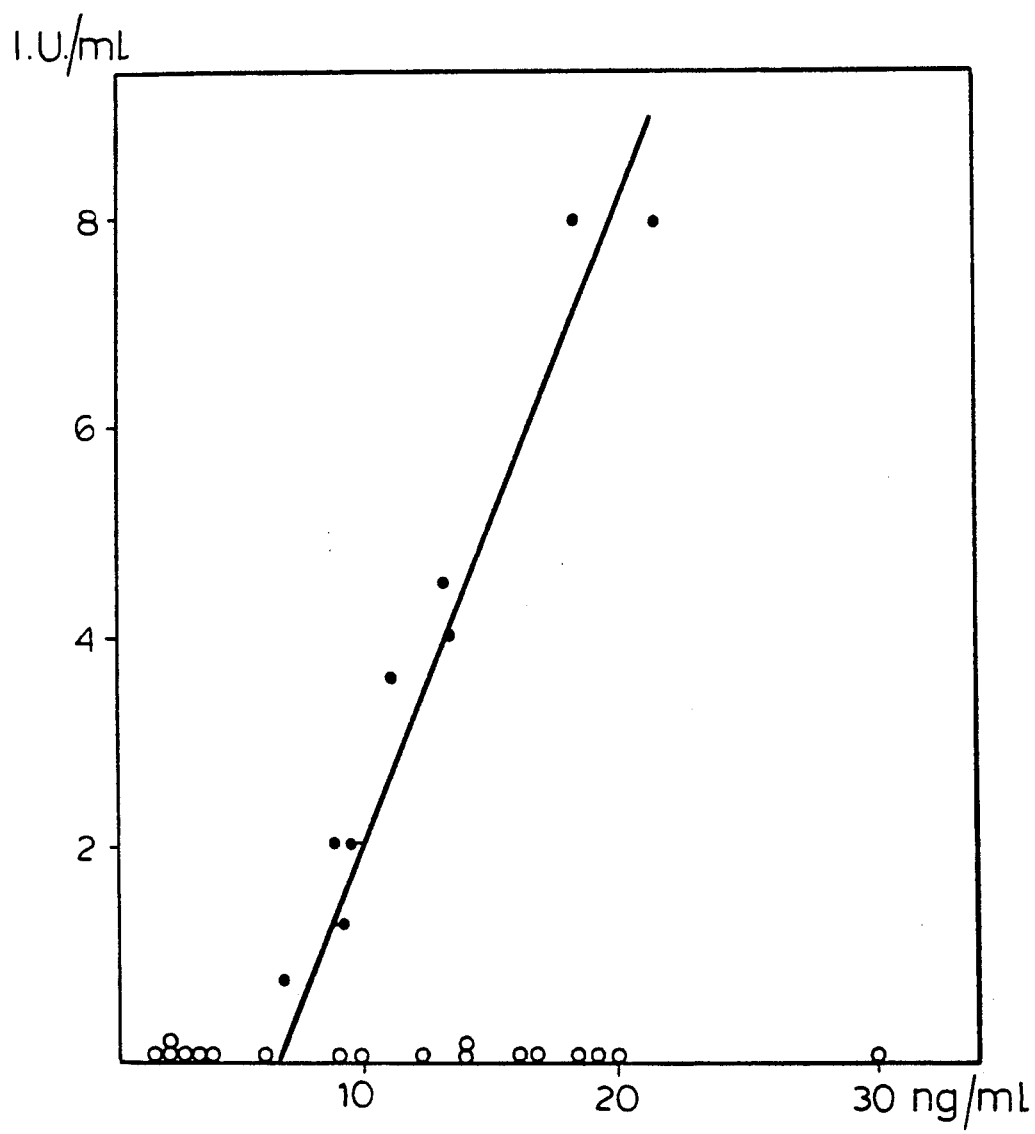
FIG. 3: Correlation between t-PA antigen, measured after the venous stasis on the abcissa ng/ml and the t-PA activity after the venous stasis on the ordinate, each per ml for normal control subjects (open triangles) and for patients with a reduced stasis activity (open circles).

In the table, the mean values and the standard deviations for t-PA activity and t-PA antigen in the case of 10 normal control subjects are indicated, and namely before and after the venous stasis:

|  | before venous stasis | after venous stasis |
| --- | --- | --- |
| t-PA antigen | 2.7 ± 0.5 | 26.6 ± 4.4 |
| t-PA activity | >0.2 | 3.7 |

Control group n = 10, average ages 29.6 ± 8.1 years.

EXAMPLE 2

System for the Determination of Function and Antigen of the Urokinase-Plasminogen Activator and the Pro-Urokinase in Biological Liquids. Micro-ELISA-plates are treated with 100 µl per dish of 0.035M sodium-bicarbonate-buffer, pH 9.6, containing a 20 µg of a polyclonal goat-antiurokinase-antibody, for two hours at 4° C. After that, they are washed three times with 3 µl per dish PBS, containing 0.05% of Tween 20. The remaining binding sites on the polyslyrene plate are after that saturated with 100 µl per dish of 1% bovine serum-albumin-solution in PBS, for 4 hours at room temperature, whereafter the plates are again washed. Thereafter, the plates can either be air-dried, lyophilized or preserved in any other suitable way.

In order to perform the determinations, after a single washing the plates are incubated for 2 hours at 37° C. with 100 µl of a u-PA-containing specimen, if necessary diluted in PBS, containing 0.5% BSA, 0.01% Tween 80, whereby the time and the temperature can vary. After that, the plates are washed again. Then, 100 µl per dish of a suited plasmin substrate, e.g. HDNLE-HHD-Lys-pNA in a concentration of 0.04 mM per liter, as well as the natural substrate Glu-plasminogen in a concentration of 500 nM per liter is added. The plates are incubated in the dark for one hour at 37° C. Afterwards, the absorption at 405 nM is measured with the reference wave-length 495 nm in a preferably two-wave spectrophotometer. If in a specimen the activity of prourokinaze is to be measured, the specimen has first to be treated with a 0.5 µM per liter of human plasma solution bound to sepharose for one hour at 37° C. in a quantity of 100 µg/ml. After removal of the plasmin-sepharose, the activity of the prourokinaze can then be measured in the same way, whereby during binding 10 units per ml of aprotinin have to be present. After determining the function, the plates are again washed and 100 µl per dish of a peroxidase-marked monoclonal antibody, e.g. MPW5UK, in a concentration of 1 µg per ml are added and the plates are incubated for 2 hours at 37° C. Subsequently, the plates are washed and a solution of 1 mg per liter of orthophenyldiamine in 0.11 mol per liter sodium phosphate, 0.05 µl citrate buffer, pH 5.85, containing 0.03% $H_2O_2$, added in an amount of 100µl. The plates are incubated in the dark for 15 minutes at room temperature and the reaction is concluded by the addition of 100 µg per dish 1.5 mol per liter sulfuric acid. The absorption is measured at 495 nm with 540 nm reference wave-length, optimally in a two-wavelength spectrophotometer. Instead of orthophenyldiamine, another suitable peroxidase substrate can be used, respectively the marking of the second antibody with another enzyme can also take place in corresponding manner.

Figure 4:
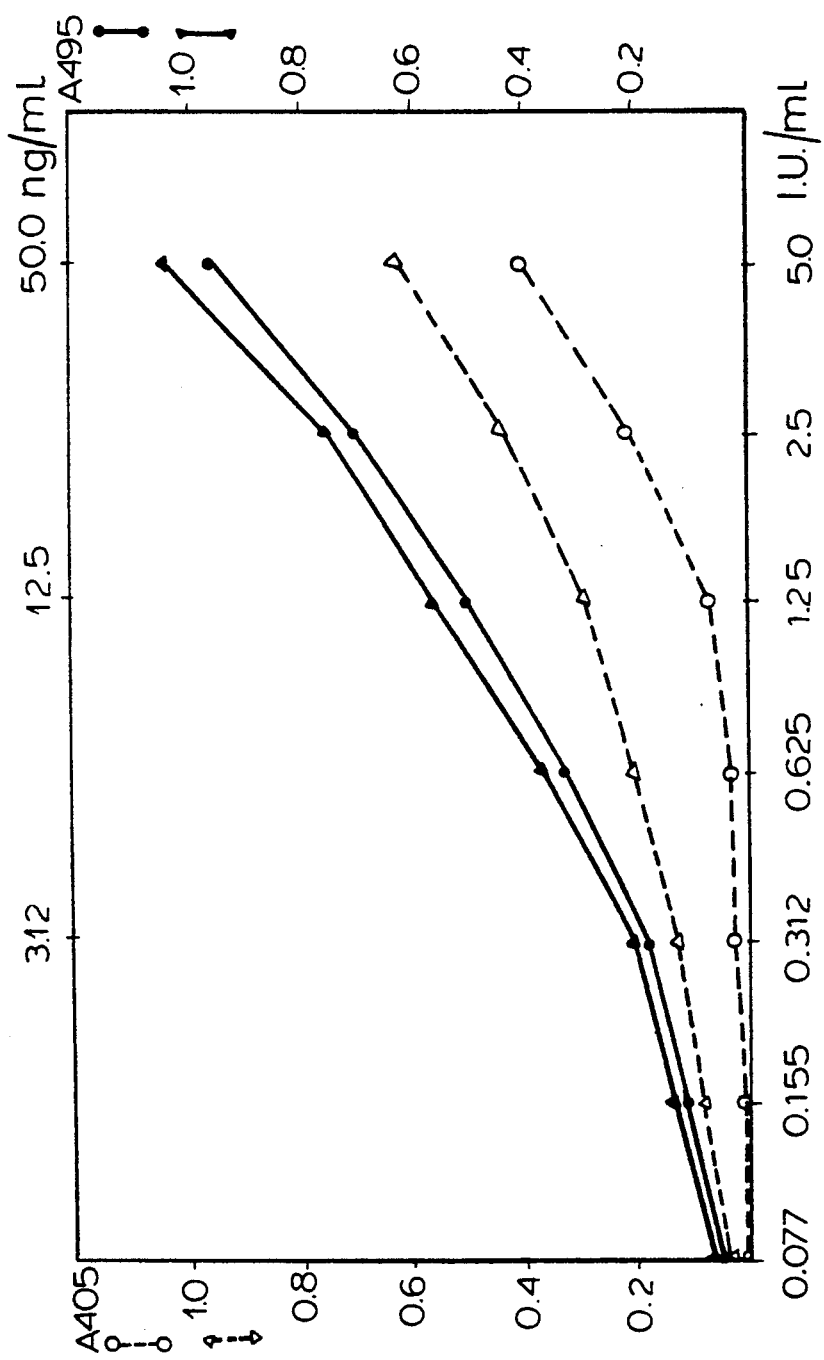
FIG. 4 is a series of curves showing Urokinase absorption values in a buffer and in plasma in an activity assay.

Standard curves for urokinase are obtained due to the fact that concentrations of 5, 2.5, 1.25, 0625, 0.312 und 0.155 and 0.0677 International Units per ml of urokinase are added and determined in the corresponding test system. The results for urokinase in buffer and plasma are indicated in FIG. 4: absorption values in the activity assay (open symbols, measured at 405nm) for u-PA in buffer (triangle) and plasma (circle), followed by the determination of the antigen level (closed symbols, absorption at 495 nm) in buffer (triangle) and plasma (circle). While the antigenic concentration of the added urokinase is identical in the buffer and in the plasma, in the plasma a clear reduction of the activity of the added urokinase occurs, which is due to the binding of a specific plasminogen activator-inhibator to the urokinase. From these data, a plasma recovery of the added urokinase of 88% for the antigen assay can be calculated, when the concentration of sodium-EDTA reaches at least 15 mmol per liter, the one of benzamidine-hydrochloride 20 mmol per liter and the one of aprotinin 10 U per ml in the specimen.

In the examination of 10 normal plasma specimens, no free u-PA activity has been found, while the average content of urokinase-antigen was 1.88±0.61 ng/ml, the interassay-variation for the activity and antigen assay was 1.9 and 6.8% and the intraassay variation was 9.6 and 4.8%.

In the examination of the urokinase level in patients with urokinase treatment for the purpose of dissolving thromboses, an increase of the urokinase antigen can be established, right towards the end of the initial urokinase administration. A typical example for 4 patients is indicated in FIG. 5.

Figure 5:
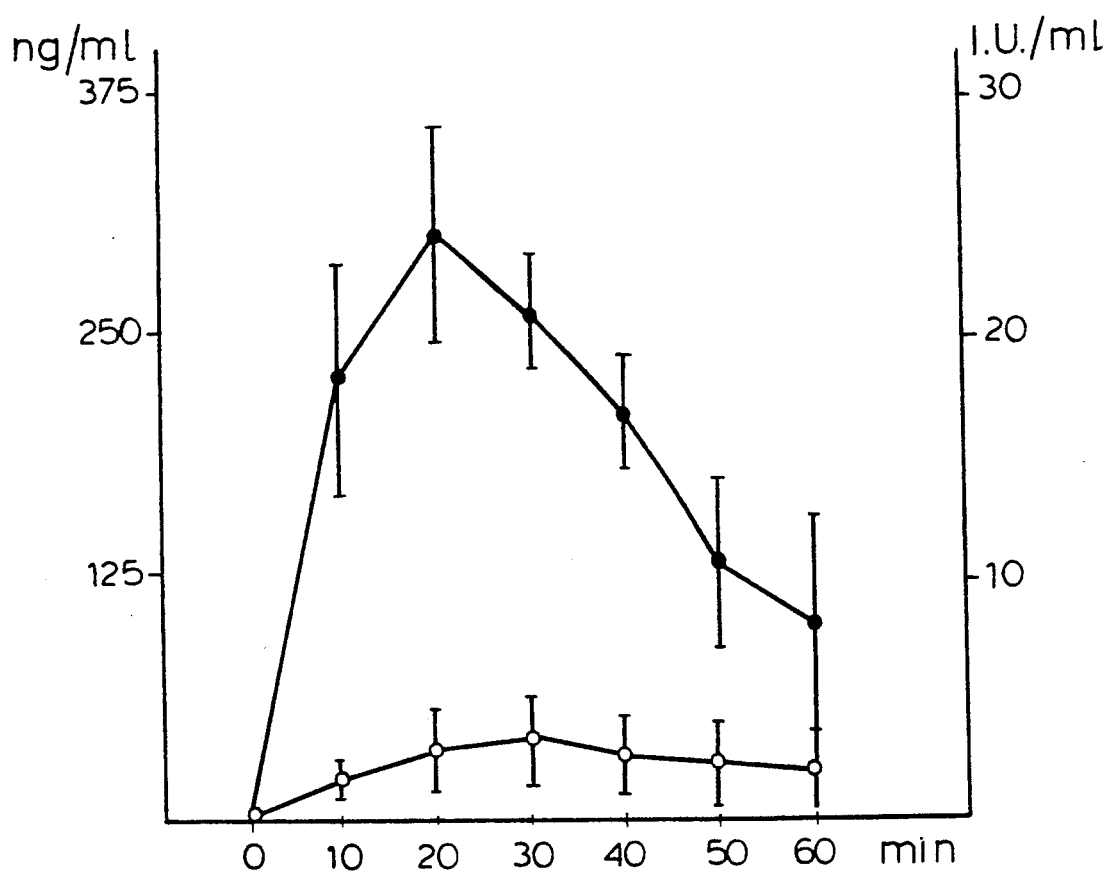
FIG. 5 is a set of two curves where Urokinase concentration and Urokinase activity are plotted against time to show that actual urokinase activity is well below urokinase concentration.

FIG. 5: Urokinase antigen (closed circle) and activity (open circle) in 4 patients during thrombolytic therapy with urokinase. Urokinase was infused in a dosage of 7.500±1.600 units per kg of body weight within 25 minutes, followed by an infusion of 1900±400 International Units per kg of body weight and hour.

I claim:

1. A process for the determination of specific activity based upon function and concentration of a plasminogen activator contained in the same single sample of blood plasma or urine, which comprises the steps of:
   (a) immobilizing the plasminogen activator by binding same to a monoclonal antibody or a polyclonal antibody that binds therewith so as to not interfere with its functional domain thereby allowing its function and concentration to be subsequently determined;

(b) quantitatively determining the biological function of the plasminogen activator immobilized during step (a) by reacting same with an enzyme substrate capable of reaction therewith;

(c) consecutively following step (b), removing the enzyme substrate by washing and quantitatively determining in said same single sample the immunological concentration of the plasminogen activator whose biological function was determined during step (b) by applying an antibody or a binding protein, specifically binding thereto, to measure total concentration of the plasminogen activator; and (d) correlating the determined function and concentration of the plasminogen activator to determine its specific activity.

2. The process defined in claim 1, wherein according to step (a), the plasminogen activator is immobilized by binding to a polyclonal antibody or monoclonal antibody itself bound to a microliter plate surface.

3. The process defined in claim 1, wherein according to step (b), the biological function of the plasminogen activator is determined by reacting same with plasminogen and determining the amount of resulting plasmin from reaction of the plasminogen and the plasminogen activator.

4. The process defined in claim 1, wherein according to step (c), the immunological concentration of the plasminogen activator is determined, using a peroxidase-marked monoclonal antibody.

5. The process defined in claim 1 wherein the plasminogen activator is tissue plasminogen activator.

6. The process defined in claim 1 wherein the plasminogen activator is urokinase.

* * * * *